(12) United States Patent
Ashok et al.

(10) Patent No.: US 12,137,976 B2
(45) Date of Patent: Nov. 12, 2024

(54) OPTICAL COHERENCE TOMOGRAPHY INSTRUMENT AND ALIGNMENT METHOD

(71) Applicant: OPTOS PLC, Dunfermline (GB)

(72) Inventors: Praveen Ashok, Dunfermline (GB); David Evans, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 744 days.

(21) Appl. No.: 17/200,800

(22) Filed: Mar. 13, 2021

(65) Prior Publication Data

US 2022/0287559 A1 Sep. 15, 2022

(51) Int. Cl.
*A61B 3/10* (2006.01)
*A61B 3/00* (2006.01)
*G01B 9/02091* (2022.01)

(52) U.S. Cl.
CPC ............ *A61B 3/102* (2013.01); *A61B 3/0008* (2013.01); *A61B 3/0025* (2013.01); *A61B 3/0041* (2013.01); *G01B 9/02091* (2013.01)

(58) Field of Classification Search
CPC ..... A61B 3/102; A61B 3/0008; A61B 3/0025; A61B 3/0041; G01B 9/02091; G01B 2290/65
USPC ........................................................ 351/205
See application file for complete search history.

(56) References Cited

U.S. PATENT DOCUMENTS

| 7,355,716 | B2* | 4/2008 | de Boer | A61B 5/0059 356/497 |
| 7,643,153 | B2* | 1/2010 | de Boer | G01B 9/02091 356/497 |
| 7,733,497 | B2* | 6/2010 | Yun | H01S 3/0071 356/497 |
| 7,830,525 | B2* | 11/2010 | Buckland | A61B 3/102 356/477 |
| 2014/0098345 | A1* | 4/2014 | Cai | A61B 3/102 351/246 |

* cited by examiner

*Primary Examiner* — Mohammed A Hasan
(74) *Attorney, Agent, or Firm* — FAEGRE DRINKER BIDDLE & REATH

(57) ABSTRACT

An ophthalmic optical coherence tomography instrument, method, and computer-readable medium. The instrument includes a scanner defining an apparent point source for scanning sample light across a subject position and an objective having a posterior imaging configuration to project the apparent point source onto a pivot point between the objective and the subject position. The objective is settable between the posterior imaging configuration for scanning the sample light across a retina of an eye at the subject position and an anterior imaging configuration for scanning the sample light across a pivot plane. An axial region from which an interferogram is detectable extends across the pivot plane while the objective is in the anterior imaging configuration. A pupil alignment method uses the anterior imaging modality to obtain a structure position of a structure of an eye's anterior segment and then an offset between the structure position and a reference position.

58 Claims, 8 Drawing Sheets

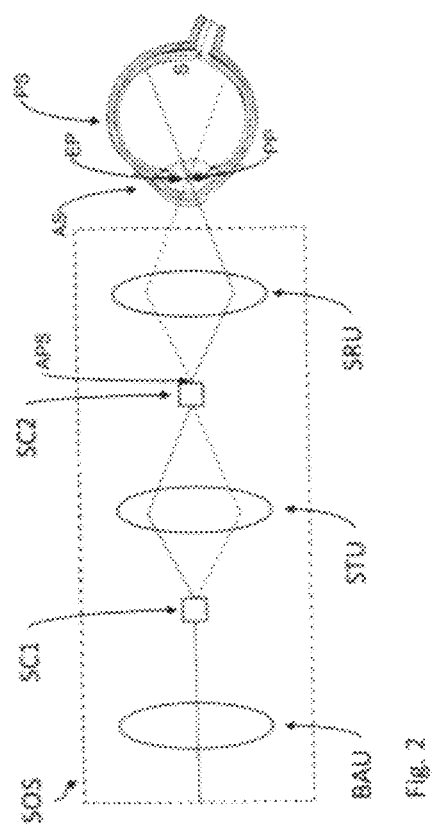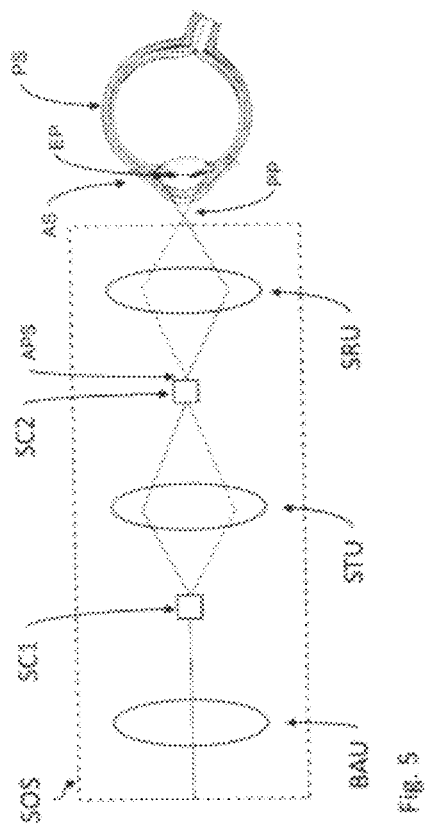

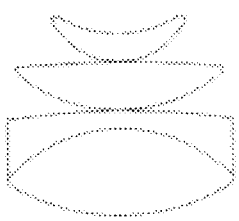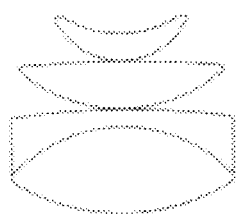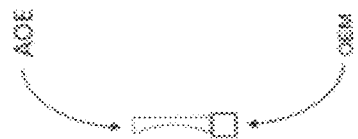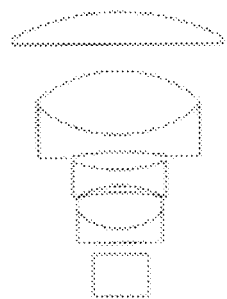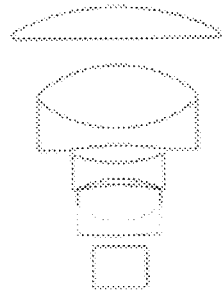

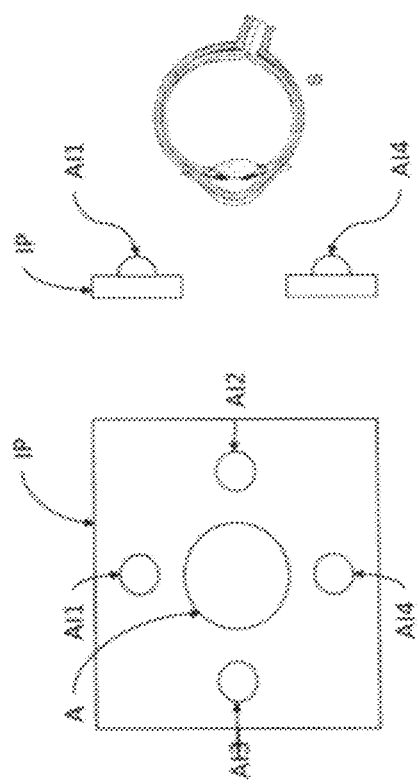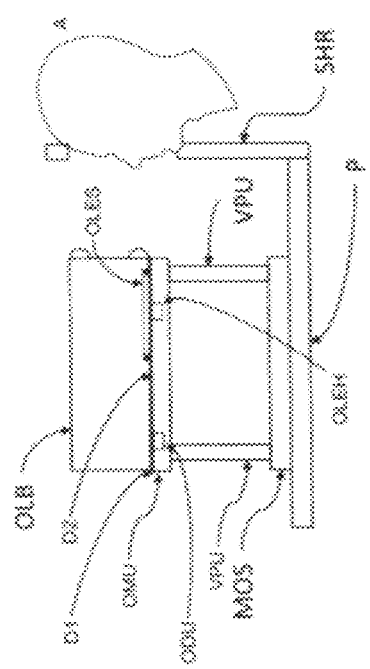

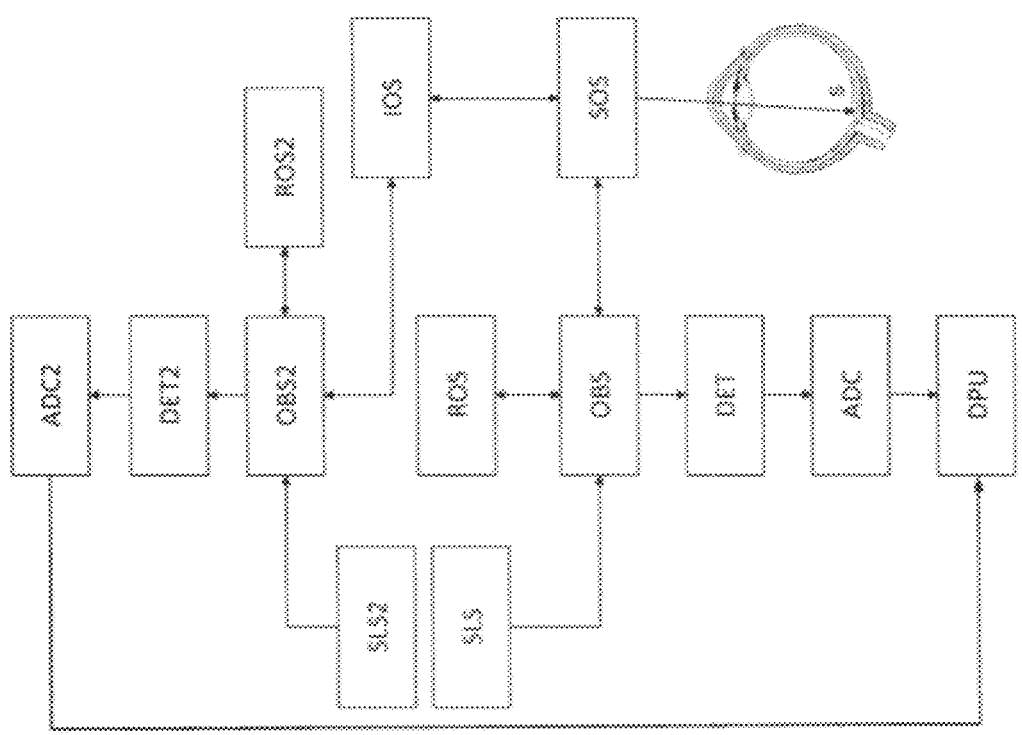

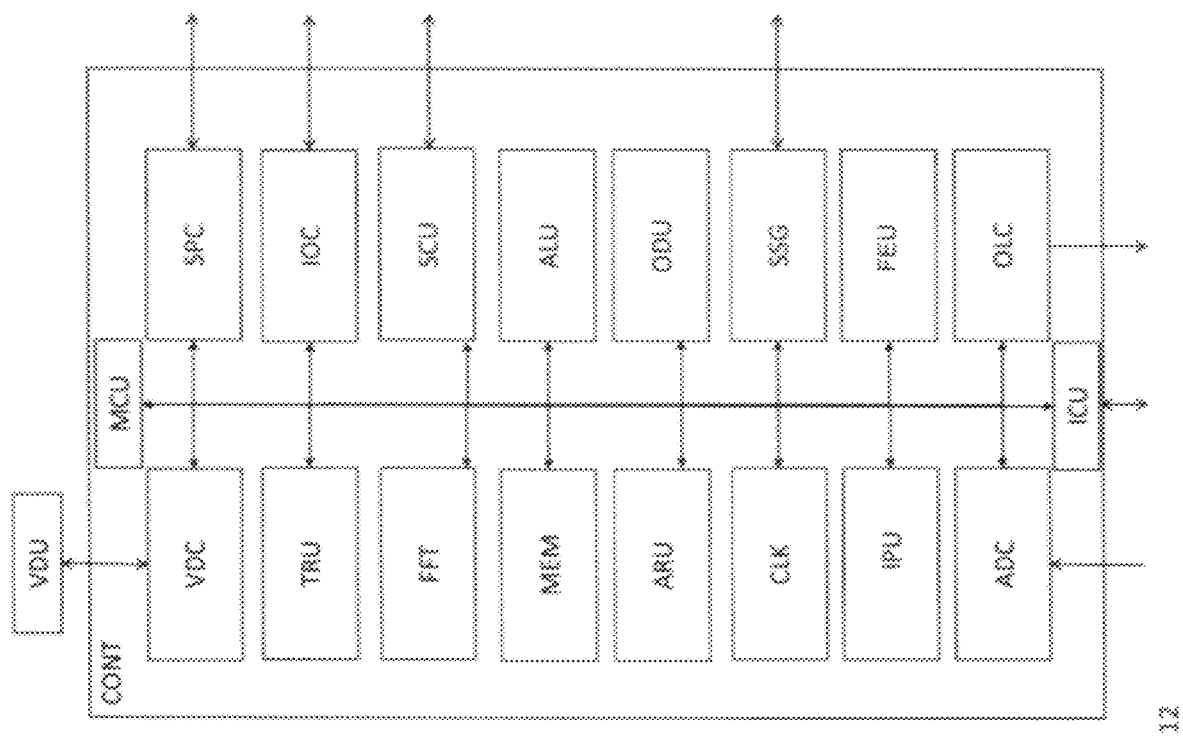

OPTICAL COHERENCE TOMOGRAPHY INSTRUMENT AND ALIGNMENT METHOD

FIELD

Example aspects herein relate to an optical coherence tomography instrument, and, more particularly, to an optical coherence tomography instrument which is capable of performing an optical coherence tomography measurement of a retina, and to an alignment method for an optical coherence tomography instrument.

BACKGROUND

Optical coherence tomography (OCT) is an imaging technique capable of obtaining high-resolution measurements and imaging of surface and subsurface structures of layered material such as, inter alia, human tissue, particularly the retina, non-invasively.

In optical coherence tomography, measurement light is split by an optical coupler, and the resulting split light is provided along two respective paths, one of which includes a so-called reference arm and another of which includes a so-called sample arm. In the sample arm, the light is directed by a sample optical system, sometimes termed a front-end optical system, to a sample under investigation, and reflected light from the sample is collected by the sample optical system and returned to the optical coupler.

In the reference arm, the light enters a reference optical system which returns the light to the optical coupler. The returning light from the sample arm and the reference arm are recombined by the coupler to generate an interference pattern. The interference pattern is recorded by a detector.

The interference pattern contains information about the optical path travelled by the reflected sample light and the magnitude of the sample light having travelled a particular optical path length. Since the wavelength of the light is selected to at least partially penetrate the sample under investigation, the interference pattern contains information about the reflectivity of the surface and subsurface structure of the sample to be investigated.

Different implementations of the optical coherence tomography technique are known in the art. One technique, termed swept-source optical coherence tomography (SS-OCT), uses measurement light, the optical frequency of which is periodically modulated in a controlled way across a defined source bandwidth. Typically, a series of rising sweeps over a defined optical frequency band are used as the modulation. A temporally-varying interference pattern signal is recorded by the detector. A Fourier transform of the recorded signal over one periodic modulation of the optical frequency of the measurement light generates an axial depth profile of the sample, with intensity corresponding to a strength of the reflection.

Scanning the measurement light one- or two-dimensionally across the surface of the sample enables an axial depth profile to be obtained for each of a plurality of points across the surface of the sample such that a two- or three-dimensional depth profile of the sample can be obtained.

A coherence length of the measurement light determines the imaging depth of the system, which is the axial depth from which interference between the sample and reference light can be obtained. Moreover, optical path lengths of the sample and reference arms determine an axial position at which the axial depth profile is obtained.

One known configuration of an optical coherence tomography instrument suitable for wide-field imaging of interior structures of the eye, particularly those which lie in a posterior segment such as the retina, is disclosed in International Publication No. WO 2014/053824 A1. In this configuration, a sample optical system includes an optical arrangement which applies a one or two-dimensional angular scan pattern to the sample beam in order to scan the sample beam across the interior of the eye.

In the known configuration, a pair of scan units which are arranged to apply an angular deflection along orthogonal axes to the sample beam are arranged at respective foci of an imaging optical system, such that a scan pivot point of a first one of the scan units is transferred onto a scan pivot point of a second one of the scan units. Thereby, a two-dimensional angular scan pattern resulting from a combination of angular deflections applied by each scan unit is applied to the sample beam exiting the second scan unit. A projection optical system is then used to project the scan pivot point of the second scan unit into the eye such that the angular scan pattern of the sample beam can access an extended range in two dimensions over a surface of an interior of the eye. By virtue of such a configuration, it is possible to obtain optical coherence tomography measurements from points on the interior of the eye that would otherwise be inaccessible.

However, in the known configuration, it is necessary to position the eye relative to the instrument such that the projected image of the scan pivot point of the second scan unit is located in at a position axially aligned with, and centred on, a pupil of the eye, which is defined by an interior edge of the iris of the eye. Deviations axially or laterally from this positioning can result in areas of the interior of the eye becoming inaccessible for measurement.

To address this, such an instrument may be provided with a pupil camera which at least partially shares an imaging optical path with the sample optical system and which images a plane containing a projected image of the scan pivot point. By observing the image recorded by the pupil camera in real time, it can be observed whether the instrument is properly positioned relative to the eye, for example by checking that the pupil is laterally centred on the scan pivot point and that the scan pivot point and the pupil are in the same plane. However, even with a high-resolution pupil camera with a shallow depth of field, this alignment method requires optical complexity, and can be slow and inaccurate.

SUMMARY

According to an example aspect herein, there is provided an ophthalmic optical coherence tomography instrument. The instrument comprises a light source arranged to generate a measurement light. The instrument also comprises a coupler arranged to split the measurement light into reference light and sample light. The instrument also includes a sample arm, comprising a front end optical system, and arranged to direct the sample light towards a subject position and to receive reflected sample light from the subject position. The instrument also includes a reference arm, comprising a return optical system, and arranged to receive the reference light and return the reference light to interfere with the reflected sample light. The instrument further comprises a detector arranged to detect an interferogram of the reflected sample light and the returned reference light.

In one example embodiment herein, the front end optical system comprises a scanner defining an apparent point source for scanning the sample light across the subject position, and, in one example embodiment herein, an objective having a posterior imaging configuration to project the apparent point source onto a pivot point on a pivot plane between the objective and the subject position. The objective is settable between the posterior imaging configuration for scanning the sample light across a retina of an eye at the subject position and an anterior imaging configuration for scanning the sample light across the pivot plane.

According to an example embodiment herein, at least one of the sample arm or the reference arm is adjustable to vary an axial region in which the sample light scans across the subject position. While the objective is set in the anterior imaging configuration, an axial region in which the sample light scans across the subject position is fixed to extend across the pivot plane, according to an example embodiment herein.

In a further example embodiment herein, the instrument further comprises a controller arranged to set the objective in one of the posterior imaging configuration or the anterior imaging configuration.

While the objective is in the anterior imaging configuration, the controller causes the scanner to scan the sample light across the pivot plane, such that a plurality of interferograms are detected by the detector, and derives a tomogram from the plurality of interferograms.

Additionally, the instrument can comprise a display unit, and the controller is arranged to cause the display unit to display the tomogram.

The controller can cause the display unit to display a reference indicating a position of the pivot point together with the tomogram.

Also in an example embodiment herein, while the objective is in the anterior imaging configuration, the controller causes the scanner to scan the sample light across the pivot plane in a plurality of scans, the plurality of scans extending two-dimensionally across the pivot plane, to obtain a plurality of tomograms.

The plurality of scans may comprise a plurality of intersecting scans having intersecting scan directions crossing the pivot plane. The plurality of scans may comprise a plurality of progressive scans progressing across the pivot plane in a direction intersecting with a common scan direction.

In one example embodiment herein, while the objective is in the anterior imaging configuration, the controller detects a presence of a structure of an anterior segment of the eye within an axial region using the tomogram.

Also in an example embodiment herein, while the objective is set in the anterior imaging configuration, the controller detects a presence of a structure of an anterior segment of the eye within a sub-region of an axial region corresponding to a reference region relating to the pivot point.

The controller also can recognise the presence of the structure within the axial region or sub-region, and actuate an offset indicator based on the recognition of the presence of the structure.

While the objective is set in the anterior imaging configuration, the controller obtains a structure position of a structure of an anterior segment of the eye at the subject position using the tomogram, in an example embodiment herein.

The controller also can determine an offset between the structure position and a reference position related to the pivot point.

According to an example embodiment herein, the structure includes one of a lens, iris, or cornea.

Also, according to an example embodiment herein, the instrument further comprises an offset indicator for indicating an offset between the structure position and the reference position, and the controller is arranged to actuate the offset indicator based on the determined offset.

In a further example embodiment herein, the instrument comprises an objective motor for adjusting an axial position of the objective based on the determined offset.

The offset may include an axial offset.

The offset may include a lateral offset.

The objective is axially movable in the instrument. By example and without limitation, the movement is from a first defined position for the posterior imaging configuration to a second defined position for the anterior imaging configuration.

According to an example embodiment herein, the first defined position is defined by a first stop or detent, the second defined position is defined by a second stop or detent, and the objective is movable manually from the first defined position to the second defined position.

Also, according to an example embodiment herein, the instrument further comprises an objective motor (e.g., a drive motor) for moving the objective axially. The controller is arranged to cause the objective motor to move the objective from the first defined position to the second defined position.

In still a further example embodiment herein, the instrument comprises an objective position detector arranged to detect an axial position of the objective at the first defined position and the second defined position, and/or to detect movement of the objective from the first defined position to the second defined position using the objective position detector.

The objective is switchable from the posterior imaging configuration to the anterior imaging configuration.

In an example embodiment herein, the objective is switchable by inserting an optical element to the objective or by removing an optical element from the objective.

Also in an example embodiment herein, the objective is arranged, in the anterior imaging configuration, to project the apparent point source onto another pivot point on another pivot plane arranged between the objective and the pivot plane.

The objective also can be arranged, in the anterior imaging configuration, as a telecentric lens to scan the sample light from the apparent point source vertically at the pivot plane.

In one example embodiment herein, the scanner comprises a first scanning element for scanning the sample light in a first direction, and a second scanning element for scanning the sample light in a second direction, and the front end optical system also comprises a transfer optical system arranged between the first and second scanning elements to generate a two-dimensional scan pattern from an apparent point source at the second scanning element.

According to an example embodiment herein, the first scanning element is located at a first focal point of the transfer optical system and the second scanning element is located at a second focal point of the transfer optical system.

According to another example aspect herein, there is provided a pupil alignment method for ophthalmic optical coherence tomography. The method comprises, in an anterior imaging modality, acquiring a plurality of optical coherence tomography interferograms from successive scans of light scanned across and reflected from an anterior segment of an eye. The alignment method also comprises deriving a tomogram of an axial region intersecting a pivot plane across which the light is scanned, based on at least one of the interferograms. The alignment method also comprises obtaining a structure position of a structure of the anterior segment of the eye at a sample position using the tomogram. The alignment method further comprises determining an offset between the structure position and a reference position related to a pivot point on the pivot plane.

In an example embodiment herein, in the acquiring, the sample light is scanned across the pivot plane to obtain the plurality of interferograms from each scan, and the deriving derives the tomogram based on the plurality of interferograms.

The method further can comprise displaying the tomogram.

Additionally, the method can comprise displaying a reference related to a position of the pivot point together with the tomogram.

In a further example embodiment herein, in the acquiring, the light is scanned across the pivot plane in a plurality of scans, the plurality of scans extending two-dimensionally across the pivot plane, and the deriving derives a plurality of tomograms based on the plurality of scans.

The plurality of scans may comprise a plurality of intersecting scans having intersecting scan directions crossing the pivot plane. The plurality of scans may comprise a plurality of progressive scans progressing across the pivot plane in a direction intersecting with a common scan direction.

Also, according to an example embodiment herein, the determining comprises recognising a presence of a structure of the anterior segment of the eye within the axial region using the tomogram.

Additionally, in an example embodiment herein, the determining comprises recognising a presence of a structure of the anterior segment of the eye within a sub-region of the axial region corresponding to a reference region relating to the pivot point.

Also, according to an example embodiment herein, the method further comprises indicating the presence of the structure within the axial region or sub-region based on the recognising of the presence of the structure.

Additionally, according to an example embodiment herein, the structure includes one of a lens, iris, or cornea.

In a further example embodiment herein, the method additionally comprises indicating the offset between the structure position and the reference position based on the determined offset.

In still a further example embodiment herein, the method also comprises adjusting an axial position of the objective based on the determined offset.

The offset may include an axial offset.

The offset may include a lateral offset.

According to an example embodiment herein, the alignment method is for an ophthalmic optical coherence tomography instrument that is operable in the anterior imaging modality or a posterior imaging modality, and the posterior imaging modality is for acquiring an interferogram from light reflected from the eye at a subject position. The posterior imaging modality projects an apparent point source for scanning light across a retina of the eye at the subject position onto the pivot point on the pivot plane, and at least one of the pivot point or the pivot plane is between the instrument and the subject position.

The anterior imaging modality and the posterior imaging modality may use a common objective.

In an example embodiment herein, the common objective is axially moved in the instrument from a first defined position for the posterior imaging configuration to a second defined position for the anterior imaging configuration.

According to another example embodiment herein, the first defined position is defined by a first stop or detent and the second defined position is defined by a second stop or detent. The common objective can be moved manually from the first defined position to the second defined position.

The common objective can be moved axially by an objective drive motor from the first defined position to the second defined position, according to an example embodiment herein.

In still a further example embodiment herein, an axial position of the common objective is detected at the first defined position and at the second defined position to detect movement of the common objective from the first defined position to the second defined position.

The method further comprises setting the common objective from an anterior imaging configuration to implement the anterior imaging modality to a posterior imaging configuration to implement the posterior imaging modality, according to an example embodiment herein.

In an example embodiment herein, the setting comprises switching the objective from the anterior imaging configuration to the posterior imaging configuration.

Additionally in an example embodiment herein, switching the objective comprises inserting an optical element to the objective or removing an optical element from the objective.

Further in an example embodiment herein, the anterior imaging modality uses a first interferometer arrangement and the posterior imaging modality may use a second interferometer arrangement.

In the anterior imaging configuration, the objective projects the apparent point source onto another pivot point on another pivot plane arranged between the objective and the pivot plane, according to a further example embodiment herein.

In the anterior imaging configuration, the common objective can scan the light from the apparent point source vertically at the pivot plane.

The anterior imaging modality and the posterior imaging modality may use a common interferometer.

In another example embodiment herein, the alignment method is for an ophthalmic optical coherence tomography instrument that is operable in a selected one of the anterior imaging modality or a posterior imaging modality. In the anterior imaging modality, the acquiring uses a first interferometer to interfere reference light and the light reflected from the anterior segment to obtain the interferograms, and the posterior imaging modality uses a second interferometer to interfere respective further reference light and further light reflected from a posterior segment of the eye to obtain at least one other interferogram.

According to still a further example embodiment herein, the deriving derives the tomogram based on at least one of (a) the interferograms obtained by the acquiring in the anterior imaging modality or (b) the at least one other interferogram obtained in the posterior imaging modality.

BRIEF DESCRIPTION OF THE DRAWINGS

These and other features, aspects, and advantages of the example aspects herein will become better understood with regard to the following descriptions, claims, and accompanying drawings. It is to be noted, however, that the drawings illustrate only several embodiments of the invention and are therefore not to be considered limiting of the scope of the invention as it can admit to other effective embodiments.

FIG. 2 shows a schematic arrangement of a sample optical system of the optical coherence tomography instrument, and a sample such as an eye.

FIG. 3 shows an optical diagram of an objective lens of the sample optical system in a posterior imaging configuration.

FIG. 4 shows an optical diagram of the objective lens of FIG. 3 in an anterior imaging configuration.

FIG. 5 shows a schematic diagram of a sample optical system in an anterior imaging configuration in which an anterior segment is scanned via a projected pivot point arranged in front of an eye, according to an example embodiment herein.

FIG. 9A shows a schematic front view of an indicator arrangement for indicating proper alignment of an eye relative to the instrument, according to an example embodiment herein;

FIG. 9B shows a schematic cross-section of an indicator arrangement for indicating proper alignment of an eye relative to the instrument, according to an example embodiment herein;

FIG. 10 shows a schematic cross-section of a positioning arrangement for positioning the objective of the instrument relative to a subject for OCT measurement, according to an example embodiment herein;

FIG. 11 shows an alternative schematic of an optical coherence tomography instrument (system) having posterior and anterior OCT measurement interferometers, according to another example embodiment herein;

FIG. 12 shows a schematic of a controller for an optical coherence tomography instrument, according to an example embodiment herein;

DETAILED DESCRIPTION

Figure 1:
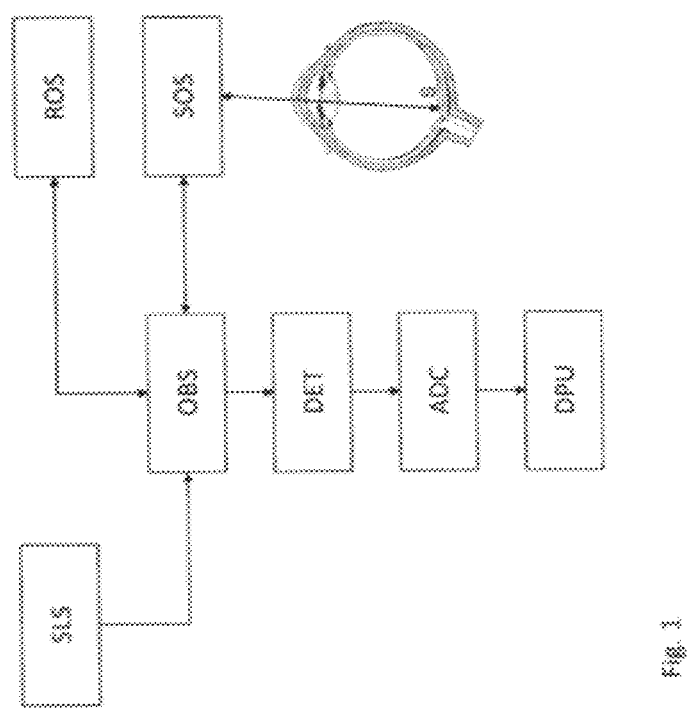
FIG. 1 shows a schematic diagram of an optical coherence tomography instrument (system) according to an example embodiment herein.

FIG. 1 is a schematic diagram of an optical coherence tomography instrument (also referred to herein as an optical coherence tomography system) constructed and operated according to an example embodiment herein. At least some components of the instrument shown in FIG. 1 form an interferometer.

In the instrument of FIG. 1, a swept light source SLS generates a beam of narrowband light with a variable centre frequency. Swept light source SLS is configured to vary a centre frequency of the narrowband light in a repetitive manner, such as by a repeated periodic frequency sweep over a defined frequency band monotonically between a lower frequency and an upper frequency. Such a frequency sweep is conventionally termed a chirp. In one example embodiment herein, swept light source SLS includes a tuneable laser or tuneable laser diode. Also in in example embodiment herein, the swept light source SLS includes an external cavity laser, an optical parametric amplifier, a Fourier-domain mode-locking laser (FDML) or a tuneable vertical cavity surface-emitting laser (VCSL). The bandwidth of swept light source SLS is selected for optimum penetration through, for example, a lens of an eye and tissues of a retina, and is in, for example, the infra-red region of the optical spectrum, for example, at wavelengths longer than 850 nm. In embodiments, example centre or longest wavelengths of the frequency sweep include 850 nm or 1050 nm. Of course, these examples are non-limiting.

The beam of narrowband light generated by swept light source SLS is directed to optical beam splitter OBS which acts as an optical coupler to split the beam of narrowband light from light source SLS into two beams. In one example embodiment herein, the splitting of the beam is symmetric, such that equal intensity is directed into two resulting beams. In another example embodiment herein, the splitting of the beam is asymmetric, such that unequal intensity is directed into two resulting beams.

In either embodiment, a first one of the resulting beams, termed a sample beam, is directed to a sample optical system SOS (also referred to herein as a "front end optical system") in a sample arm. The sample optical system SOS includes optical components to shape and direct the light beam to a sample S, such as, by example a retina, and to collect reflected light of the sample beam (i.e., light reflected from the sample S) and to return it to the optical beam splitter OBS. The returning reflected light of the sample beam follows essentially a same path of the sample arm to the optical coupler (e.g., optical beam splitter OBS) as the sample beam, but in a reverse direction.

A second one of the resulting beams, also referred to herein as a reference beam, is directed to a reference optical system ROS in a reference arm. The reference optical system ROS (also referred to herein as a "return optical system") reflects and returns the reference beam to the optical beam splitter OBS. At the optical beam splitter OBS, returning reflected light of the sample beam (i.e., light reflected from the sample S) and the returning reference beam (i.e., the reference beam returned from the reference optical system ROS) are combined so as to interfere with one another and are directed as interfering beams (representing an interferogram) to detector DET.

Detector DET, which, in one example embodiment herein, is a photodetector such as a photodiode or an avalanche photodiode, converts an optical intensity of the interfering beams to provide a resulting converted signal in the form of, for example, an electrical signal such as a voltage or current. In one example embodiment herein, the resulting converted signal is a time-varying analogue signal. After being output by the detector DET, the resulting converted signal can be recorded in a time-varying manner, as will be described below, wherein a recorded version of the signal constitutes a recorded interferogram between the returning reflected light and the returning reference beam with respect to the optical frequency of the narrowband light from the swept light source SLS.

In the example embodiment depicted in FIG. 1, an analogue to digital converter ADC periodically samples and quantises the signal output by the detector DET with a defined (predetermined) sample frequency, and then digital values of the quantised and sampled signal are provided to a data processing unit DPU wherein the values are recorded. In one example embodiment herein, the data processing unit DPU performs a Fourier transform, such as a fast Fourier transform, on the time-varying quantised and sampled signal values obtained from analogue to digital converter ADC to generate an axial depth profile.

In one example embodiment herein, swept light source SLS has relatively low coherence length such that the interference between the returning reflected light and the returning reference beam is only possible for reflected light which is reflected from a relatively narrow axial depth range along the sample beam, centred on an axial position corresponding to an optical path length of the reference arm. A Fourier transform of the sampled signal recorded at the data processing unit DPU generates a profile of reflectivity at a point interrogated by the sample beam against depth within the axial depth range.

In the instrument of FIG. 1, the optical path length of the reference arm is adjusted to set an axial position of the axial depth range to correspond to a position of a surface of the sample S under investigation. For example, a movable mirror M (not shown in FIG. 1) included in reference optical system ROS can alter the optical path length travelled by light in the reference arm. In other example embodiments herein, other methods known in the art (or later developed) for introducing variable optical delay can be employed instead.

In an example embodiment herein, sample optical system SOS includes scanning optics which can cause a pivoting of the sample beam about a pivot point PP located in an anterior segment AS of the eye (e.g., sample S) in order to scan the sample beam across a wide field of the retina located in a posterior segment PS of the eye. A schematic representation of sample optical system SOS according to the present example embodiment is shown in FIG. 2.

In the configuration of FIG. 2, the sample beam enters on a left-hand side from the optical beam splitter OBS and is shaped by beam adjustment unit BAU. For example, the beam may be expanded or narrowed, a profile of the beam may be adjusted, a degree of convergence or divergence of the beam may be adjusted, and a lateral positioning of the beam may be adjusted.

The beam adjusted by beam adjustment unit BAU then arrives at first scan unit SC1. First scan unit SC1 introduces a periodic angular deviation to the beam in a first plane, such that the beam scans over a first angular range. First scan unit SC1 includes, for example and without limitation, an oscillating plane mirror such as a galvanometer scanner, an MEMS mirror, a rotating mirror, a prism or polygon scanner or a resonant scanner.

The deviated beam from the first scan unit SC1 is then received and transferred by scan transfer unit STU to second scan unit SC2. Scan transfer unit STU is an imaging optical system, the first scan unit SC1 can be arranged at one focal point, and the second scan unit SC2 can be arranged at another focal point.

Similar to first scan unit SC1, second scan unit SC2 also introduces a periodic angular deviation to the beam, such that the beam scans over a second angular range in a second plane, which intersects with the first plane. The first and second planes may be orthogonal, in one example embodiment herein. Also, according to an example embodiment herein, the second scan unit SC2 includes an oscillating plane mirror such as a galvanometer scanner, an MEMS mirror, a rotating mirror, a prism or polygon scanner or a resonant scanner.

As a result of the arrangement of scan transfer unit STU between first scan unit SC1 and second scan unit SC2, the sample beam leaving second scan unit SC2 scans angularly in two dimensions from an apparent point source APS located at second scan unit SC2.

In an alternative example embodiment herein, however, only a single scan unit is employed (as compared with the first scan unit SC1 and the second scan unit SC2 shown in in FIG. 2) which is capable to introduce an angular deviation in two intersecting directions to the sample beam so as to scan directly the sample beam two-dimensionally. In such a case, no scan transfer unit is necessary.

In an example embodiment herein in which the scan transfer unit STU is employed, the scan transfer unit STU includes and/or is implemented as a catadioptric, catoptric, or a dioptric optical system, and, in one example embodiment herein, the scan transfer unit STU comprises an elliptical mirror. For convenience, one or a combination of two or more of the first scan unit SC1, second scan unit SC2, and the scan transfer unit STU, also is referred to herein as a "scanner", and, in the example embodiment in which only the single scan unit is employed, that single scan unit also is referred to as a "scanner".

According to an example embodiment herein, in order to access a wide region of an interior of the eye (i.e., sample S) with the two-dimensionally angularly scanning sample beam, scan relay unit SRU is included in the sample optical system SOS. The scan relay unit SRU is a further imaging optical system which projects the apparent point source arranged at second scan unit SC2 into the eye, so as to be centred on and located within a pupil EP of the eye (i.e., sample S). As can be appreciated in view of FIG. 2, such positioning ensures that the two-dimensionally scanning sample beam is able to scan a wide range of the interior of the eye. In an example embodiment herein, the scan relay unit SRU includes a catadioptric, catoptric, or dioptric optical system, and, in one embodiment, the scan relay unit STU may comprise an elliptical mirror.

FIG. 3 shows an example optical configuration that, in one example embodiment herein, can form part of scan relay unit SRU, wherein the optical configuration is represented in the form of an objective lens (also referred to herein as an "objective"). The optical configuration shown in FIG. 3 contains a plurality of lens elements which sequentially act on the sample beam so as to project the sample beam into the eye (i.e., sample S) while minimising or avoiding aberration to a desired extent. The lens elements may be contained within an objective lens barrel OLB, which is shown schematically in FIG. 10.

Certain optical elements of the optical configuration shown in FIG. 3 can be movable in order to adjust a divergence or convergence of the sample beam, to adjust an axial positioning of the sample beam, or to adjust a width of the sample beam. In one example embodiment herein, the objective lens optical configuration shown in FIG. 3 can include an anti-vibration lens element which is laterally movable to compensate for vibrations. Also, according to an example embodiment herein, the objective lens optical configuration shown in FIG. 3 includes dioptric lens elements, diffractive lens elements, and/or birefringent lens elements. The optical configuration shown in FIG. 3 is, however, exemplary, and, in some example embodiments herein, it is sufficient that the objective lens is capable to project a full scanning range of the sample beam through the pivot point arranged at the pupil into the eye. To this end, in an example embodiment herein it can be useful to employ, for the objective lens, an objective lens having a high numerical aperture, although this example is not limiting to the scope of the invention.

It should be noted that the optical configuration shown in FIG. 3 is merely exemplary, and may be varied as appropriate based on predetermined operating criteria. One exemplary optical configuration corresponding to that represented in FIG. 3 is shown in Table 1 below. That is, in one example embodiment herein, sequential components of the optical configuration shown in FIG. 3 each have a corresponding respective radius and thickness represented in sequence in Table 1, although this example is not limiting.

Also in one example embodiment herein, the optical configuration of objective lens as shown in FIG. 3 is configured to scan the sample beam across a posterior segment of the eye, but it can switched or otherwise controlled to scan the sample beam across the anterior segment of the eye.

Such switching may be performed, for example, by introducing one or more additional optical elements AOE into the configuration (for example, within scan relay unit SRU) at a defined position, as shown in FIG. 4.

In the configuration of FIG. 4, the optical configuration of the objective lens is configured to scan the sample beam across an anterior segment of the eye. When the additional optical element is introduced, the exemplary optical configuration corresponding to that represented in FIG. 3 may change to the configuration as shown in Table 2. In other words, in one example embodiment herein, sequential components of the optical configuration shown in FIG. 4 each have a corresponding respective radius and thickness represented sequentially in Table 2, although this example is not limiting.

TABLE 1

| No. | Radius | Material (Glass) | Thickness |
|-----|--------|------------------|-----------|
| 1 | Infinity | J-SF03HS | 2.53E+01 |
| 2 | Infinity | | 7.06E+00 |
| 3 | 3.27E+02 | J-FK5 | 9.00E+00 |
| 4 | 3.71E+01 | J-SF03HS | 2.30E+01 |
| 5 | −1.17E+02 | | 4.05E+00 |
| 6 | −5.50E+01 | J-SF03HS | 1.00E+01 |
| 7 | 7.92E+01 | | 1.09E+01 |
| 8 | −1.82E+02 | J-SF03HS | 1.10E+01 |
| 9 | 7.89E+01 | J-LASF016 | 4.00E+01 |
| 10 | −7.89E+01 | | 1.66E+01 |
| 11 | Infinity | J-LASKH2 | 2.00E+01 |
| 12 | −1.41E+02 | | 1.47E+02 |
| 13 | 1.30E+02 | H-ZK3 | 5.50E+01 |
| 14 | −9.41E+01 | J-SF03HS | 1.10E+01 |
| 15 | −4.84E+02 | | 5.00E−01 |
| 16 | 9.74E+01 | J-PSK03 | 3.01E+01 |
| 17 | −7.38E+02 | | 5.00E−01 |
| 18 | 4.64E+01 | J-LASF08A | 1.73E+01 |
| 19 | 7.00E+01 | | 2.50E+01 |
| 20 | Infinity | | 0.00E+00 |

TABLE 2

| No. | Radius | Material (Glass) | Thickness |
|-----|--------|------------------|-----------|
| 1 | Infinity | J-SF03HS | 2.53E+01 |
| 2 | Infinity | | 7.06E+00 |
| 3 | 3.27E+02 | J-FK5 | 9.00E+00 |
| 4 | 3.71E+01 | J-SF03HS | 2.30E+01 |
| 5 | −1.17E+02 | | 4.05E+00 |
| 6 | −5.50E+01 | J-SF03HS | 1.00E+01 |
| 7 | 7.92E+01 | | 1.09E+01 |
| 8 | −1.82E+02 | J-SF03HS | 1.10E+01 |
| 9 | 7.89E+01 | J-LASF016 | 4.00E+01 |
| 10 | −7.89E+01 | | 1.66E+01 |
| 11 | Infinity | J-LASKH2 | 2.00E+01 |
| 12 | −1.41E+02 | | 3.30E+01 |
| 13 | −5.17E+01 | N-BK7 | 5.00E+00 |
| 14 | Infinity | | 1.09E+02 |
| 15 | 1.30E+02 | H-ZK3 | 5.50E+01 |
| 16 | −9.41E+01 | J-SF03HS | 1.10E+01 |
| 17 | −4.84E+02 | | 5.00E−01 |
| 18 | 9.74E+01 | J-PSK03 | 3.01E+01 |
| 19 | −7.38E+02 | | 5.00E−01 |
| 20 | 4.64E+01 | J-LASF08A | 1.73E+01 |
| 21 | 7.00E+01 | | 2.50E+01 |
| 22 | Infinity | | 0.00E+00 |
| 23 | 7.72E+00 | | 0.00E+00 |

Such switching may also be performed, for example, by at least one or more of removing one or more such additional optical elements or other optical elements, by replacing one or more optical elements, or by moving each of one or more optical elements of the objective lens from a first position to a second or other position. In an example embodiment herein, such movement includes axially displacing one or more optical elements of the objective lens.

For example, in one example embodiment, the additional optical element or element may be mounted on a movable mount or mounts OEM, which may be actuated manually or under automated control to introduce, remove, or move the one or more optical elements between one or more respective first positions and one or more respective second positions. Such mounts can include, for example, translatable or rotatable stages, flip mounts, or turrets. In other example embodiments, the additional optical element or elements may be mounted in one or more cartridges which are to be inserted into the optical path. Automatic actuation may be facilitated by, for example, linear or rotational motors or other actuators (not shown).

In the above example embodiment, the additional optical element or elements have been exemplified as refractive optical elements. However, in an alternative example embodiment, the additional optical element or elements may be provided as reflective optical elements which introduce additional optical path length to the light propagating inside the objective lens. In further example embodiments, additional reflective optical elements may function to divert light propagating inside the objective lens from an original optical path through a further optical system before returning to the original optical path.

One exemplary effect of switching the optical configuration of the objective lens from a posterior imaging configuration (e.g., a first interferometer configuration or arrangement) to an anterior imaging configuration (e.g., a second interferometer configuration or arrangement) can be appreciated, for example, by comparing FIG. 2 and FIG. 5. In particular, when the objective lens included in scan relay unit SRU of sample optical system SOS is switched from a posterior imaging configuration such as that shown in FIG. 2 to an anterior imaging configuration such as that shown in FIG. 5, the pivot point PP from which the scanning sample beam appears to originate is displaced leftwards, closer to the sample optical system SOS, and away from an axial position at which it was previously located. Thereby, as represented in FIG. 5, the sample beam may be scanned across the anterior segment of the eye (e.g., sample S), and, in particular, may be scanned across a pivot plane which previously contained the apparent point source at the pivot point in the posterior imaging configuration represented in FIG. 3.

Figure 6:
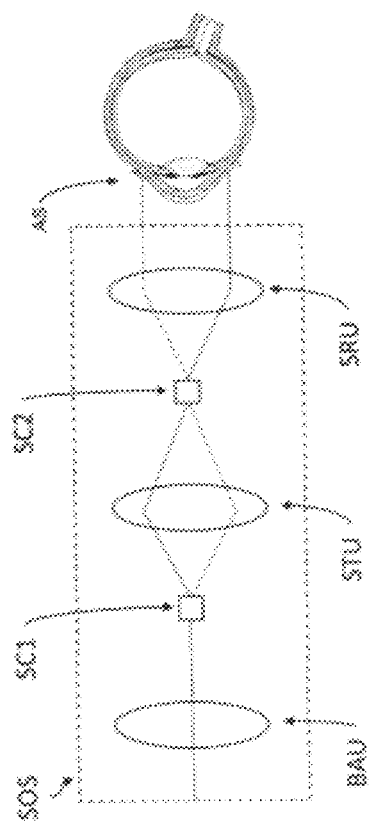
FIG. 6 shows a schematic diagram of a sample optical system in an anterior imaging configuration in which the anterior segment is scanned in a telecentric manner, according to an example embodiment herein.

Another exemplary effect of switching the optical configuration of the objective lens of sample optical system SOS from the posterior-imaging configuration to the anterior-imaging configuration can be understood by, for example, comparing FIG. 2 and FIG. 6. In particular, in the FIG. 6 configuration, the anterior imaging configuration of the objective lens is a telecentric configuration, in which an angular scan pattern of the sample beam at second scan unit SC2 is transformed into a laterally-scanning mode in which the sample beam remains parallel to a given direction, such as that in which an optical axis of the objective lens extends, while scanning across the anterior segment. The sample beam intersects the pivot plane vertically, that is, at a normal to the pivot plane, and scans across the pivot plane while remaining normal to the pivot plane.

When acquiring OCT measurements of a retina, the optical delay introduced in reference optical system ROS can be continually adjusted on a feedback basis in order to place an axial region in which OCT measurements are obtained across a region of interest of the interior of the eye. However, when the sample optical system is placed in an anterior imaging configuration, the optical delay may be fixed. For example, the optical delay (e.g., of reference optical system ROS) may be fixed by fixing a position of a displaceable return mirror of the reference optical system ROS, such that an axial region in which the OCT measurements are obtained extends across an expected position of a pivot plane containing an expected position of a pivot point in the posterior imaging configuration. In particular, the optical delay may be fixed such that the expected position of the pivot plane is at a defined axial position in the axial region. Thereby, when the interferogram is transformed to generate a depth profile, the position on the depth profile corresponding to the expected position of the pivot plane is well-defined and fixed between successive measurements.

Figure 7B:
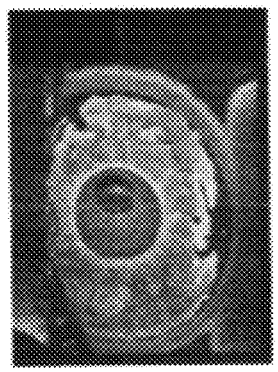
FIG. 7B shows an image representing a C-scan across the anterior segment of the eye.
Figure 7A:
FIG. 7A shows an image representing a B-scan across the anterior segment of the eye.

In such a configuration, OCT measurements may be acquired which show the positioning of the anterior structures of the eye relative to the expected position of the pivot plane. For example, a B-scan, or two-dimensional tomogram, may be obtained by successively scanning the sample beam linearly across the anterior segment of the eye while obtaining A-scans, which are axial reflectivity depth profiles obtained as Fourier transforms of the interferogram acquired by detector DET and/or data processing unit DPU. An example of such a B-scan is shown in FIG. 7A, showing a location of the pupil in the axial region.

Moreover, by assembling multiple such B-scans taken along different scan lines crossing the anterior segment, a three-dimensional or volumetric tomographic dataset can be obtained by the instrument(s) herein and displayed on a display unit (e.g., a video display unit VDU shown in FIG. 12). Tomographic slices can be obtained through the data set as image data along arbitrary planes. By taking a transverse slice along the expected pivot plane, a so-called C-scan is acquired, and lateral positioning of structures in the anterior segment of the eye in the expected pivot plane can be determined from the slice. A C-scan can also be obtained directly from the axial profiles, by assembling an image from reflectivity values acquired at a particular depth, without the need to assemble and then slice a volumetric dataset. Such a transverse slice is shown in FIG. 7B, with the depicted arrow showing a lateral displacement of the pupil from a centre of the expected pivot plane defined by the expected position of the pivot point depicted by the intersection of the dotted lines.

By acquiring B-scans at one or more directions crossing the expected pivot plane, an offset of the pupil of the eye from the expected pivot point can be determined. This can, for example, be performed visually by an operator, by displaying the B-scans on a display unit (e.g., a video display unit VDU shown in FIG. 12) of the OCT instrument. In this mode of operation, it can be useful to acquire B-scans repeatedly at multiple intersecting directions crossing the expected pivot plane, for example, at two orthogonal directions, or at equally-spaced angular intervals. By displaying such B-scans simultaneously, for example, side-by-side, on a visual display unit VDU of the OCT instrument, an amount of lateral offset of the pupil relative to the pivot point at the centre of the image can be determined visually in two or more intersecting lateral directions, as well as along the axial direction.

Moreover, by obtaining transverse slices through a volumetric dataset, such as C-scan slices, at a plane through the expected pivot point and/or through planes offset axially from the pivot point, lateral and axial offset of the pupil relative to the expected pivot point can be determined visually in horizontal and vertical lateral directions simultaneously. Advantageously, for such measurements, the angular deflections of the scan pattern in each plane are symmetric about the optical axis of the objective lens.

When the offset of the pupil of the eye from the expected pivot plane is determined visually, for example, by an operator of the instrument, the operator of the instrument may give instructions to the subject, or, alternatively, may make manual adjustments to the instrument or to the positioning of the subject to better align the pupil of the eye with the expected pivot plane when the instrument is in the posterior imaging configuration. For example, the operator may instruct the subject of the measurement to move the head to obtain better alignment, or may manually adjust a subject headrest or other positioning device which is used to comfortably locate the subject of the measurement relative to the objective lens of the instrument. Alternatively, the operator may manually adjust the position of the objective lens of the instrument relative to the subject, to better align the pupil of the eye with the expected position of the expected pivot plane.

Once the pupil of the eye is sufficiently well aligned with the expected pivot plane, the objective lens may be set to the posterior imaging configuration. As a result of the prior alignment performed with the objective lens set in the anterior imaging configuration, the pivot point is properly located relative to the pupil of the eye, and high-quality measurements may be obtained. For example, interferograms may be obtained at a variety of points across a scanline, a B-scan tomogram may be obtained from a sequence of interferograms, and the scans may be repeated at different lines across the interior surface of the eye in order to obtain a volumetric dataset from which, e.g., C-scans can be obtained. C-scans can be displayed on a display unit (e.g., a video display unit VDU shown in FIG. 12).

When the offset of the pupil of the eye from the expected pivot plane is to be determined visually, it can be useful if image-processing techniques are used to enable easy identification of relevant anatomical structure in the eye. Moreover, it can be useful if references are applied to the display of the instrument to indicate the position of the expected pivot point laterally and axially, to permit more accurate alignment.

Figure 8B:
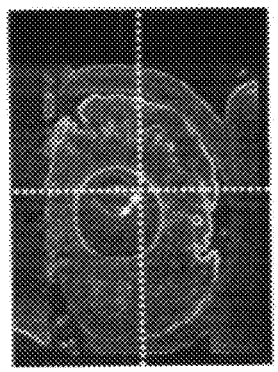
FIG. 8B shows a representation of an alignment display displaying an alignment image based on the image of FIG. 7B with references indicating alignment of an expected position of a pivot point and an offset vector.
Figure 8A:
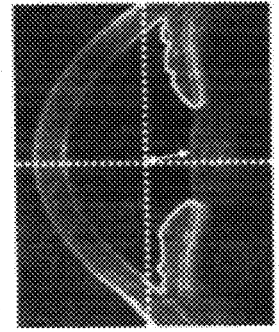
FIG. 8A shows a representation of an alignment display displaying an alignment image based on the image of FIG. 7A together with references indicating alignment of an expected position of a pivot point and an offset vector.

For example, as shown in FIG. 8A, an edge-detection algorithm can be used to detect boundaries in the data, thereby to more clearly indicate the boundaries of the pupil. As may be seen in FIG. 8A, application of an edge-detection algorithm to the B-scan shown in FIG. 7A produces a bright outline of the iris, which may be used properly to align the pupil to the expected position of the pivot point. As may also be seen in FIG. 8A, horizontal and vertical gradated reference marks, for example representing respectively the pivot plane and the optical axis of the objective, may be overlaid on the image in the form of an alignment reticle, a crossing point of which indicates the expected position of the pivot point in the posterior measurement configuration.

A similar display is shown in FIG. 8B, in which an edge-detection algorithm has been applied to the C-scan slice shown in FIG. 7B to produce a bright outline of the iris, which again may be used properly to align the pupil to the expected position of the pivot point. Again, shown in FIG. 8B, horizontal and vertical gradated reference marks, for example representing respectively the optical axis of the objective and the pivot plane, are overlaid on the image, the crossing point of which indicates the expected position of the pivot point in the posterior measurement configuration.

Furthermore, predetermined image-processing techniques may be used to automatically obtain an offset of the expected position of the pivot point relative to the pupil.

For example, by using image-processing techniques to identify converging edges in the B-section shown in FIG. 7A, the interior rim of the iris can be identified, and thus a chord of the pupil in the plane of the B-scan image may be determined. An axial offset may, for example, be defined as a distance between the expected position of the pivot point and an intersection of this chord with a line projected in the axial direction through the pivot point. Alternatively, an axial offset may, for example, be defined as the axial distance between a midpoint of this chord and the expected position of the pivot point.

Similarly, a lateral offset may be defined as a distance between the midpoint of the cord of the iris in the plane of the B-scan image and an intersection of this chord with a line projected in the axial direction through the expected position of the pivot point. Alternatively, an axial offset may, for example, be defined as the lateral distance between the midpoint of this chord and the expected position of the pivot point.

Similar determinations of a lateral offset in horizontal and vertical directions may be performed on the C-section shown in FIG. 7B. For example, a pupil centre may be approximated as an intersection of a major and minor axis of an ellipse fitted to the inner edge of the iris. A horizontal and vertical offset of the centre of the pupil relative to the expected position of the pivot point, represented by a centre of the image corresponding to the optical axis of the objective lens, may equivalently be determined.

Thereby, one or more offsets of the expected position of the pivot point relative to pupil may be displayed to the operator, for example, in the lateral and/or axial directions, as one or more measurements, for example in micro-metres, on the display unit (e.g., a video display unit VDU shown in FIG. 12) of the OCT instrument. In one configuration, the measured offset may be displayed overlaid with the B-scan or C-scan image.

Alternatively or additionally, the obtained offsets may be used to provide feedback to the operator or the subject for proper positioning of the eye relative to the instrument by appropriate indicators.

For example, as shown in FIG. 9A, an indicator panel IP may be provided having an aperture A, and a plurality of alignment indicators AI1, AI2, AI3, and AI4, arranged around the aperture A so as to be observable in peripheral vision of the subject. In the example embodiment illustrated in FIG. 9A, four alignment indicators AI1, AI2, AI3, and AI4 are shown at equally spaced angular intervals, such as, by example only, 90° intervals, around a centre of aperture A. The aperture A and alignment indicators AI1, AI2, AI3, and AI4 each are represented as being circular in shape. The alignment indicators may be, for example, LED or OLED indicators, or lamps. However, in other example embodiments herein, other arrangements, angular intervals, and shapes of the aperture and alignment indicators may be provided. FIG. 9B shows a positioning of an eye of a subject relative to a cross-sectional view of the indicator panel IP, the cross section passing through and thus showing two alignment indicators AI1, AI3.

According to an example embodiment herein, the OCT instrument is configured to provide visible feedback to the subject as to the proper positioning of the eye relative to the objective lens of the instrument using the aperture indicators AI1, AI2, AI3 and AI4. For example, the OCT instrument, and more particularly, the data processing unit DPU, may be configured to change a visible (or otherwise perceptible) state of each of alignment indicators AI1, AI2, AI3 and AI4 based on the axial and lateral offset of the pupil of the eye relative to the expected position of the pivot point obtained as described above. Such visible states of alignment indicators AI1, AI2, AI3 and AI4 may include illumination, non-illumination, flashing, steady-state, and one or more different colours, such as red, green and blue. In other words, individual ones of the alignment indicators AI1, AI2, AI3 and AI4 can be controlled by a controller (e.g., a data processing unit DPU, and/or controller CONT of FIG. 12 described below) based on the axial and lateral offset to cause the indicator(s) to become illuminated, non-illuminated, to flash, attain a steady-state, and/or to have one or more colours, corresponding to the offset(s), depending on predetermined operating criteria. The illumination or other states of the alignment indicators AI1, AI2, AI3 and AI4 can guide the subject to a proper positioning of the eye relative to the objective lens of the instrument.

For example, if a lateral offset is determined such that the eye should be moved toward the right for proper alignment, aperture indicator AI2 may be placed in a flashing configuration with a first colour, such as green. Simultaneously, aperture indicator AI4 may be placed in a flashing configuration with a second colour, such as red. The rate of flashing may indicate the offset, with a slower rate of flashing, for example, indicating a smaller offset. The subject is thus instructed to move their head laterally in a direction toward the green flashing alignment indicator until the alignment indicator either reaches steady-state or is alternatively extinguished. Whereas alignment indicators AI2 and AI4 may thus be used for horizontal alignment, alignment indicators AI1 and AI3 may similarly be used for vertical alignment, although the present example is not limiting.

For axial alignment, a separate indicator may be used. Such an indicator may be, for example, an audible indicator output by an output user interface, wherein, for example, the audible indicator includes, in one example embodiment herein, a pulsed tone indicating misalignment, a rate of pulsing of the tone and/or a pitch of the tone indicates an amount of offset and/or a direction of offset. Alternatively, once lateral alignment is achieved, the alignment indicators AI1, AI2, AI3 and AI4 can be configured to together provide feedback to the subject for axial alignment by, for example, together flashing to indicate axial offset, with the rate of flashing indicating the amount of offset, and colour, such as red and green, indicating required forward or backward movement to correct the axial offset.

In some example embodiments herein, a predetermined acceptable deviation of offset is defined, in the form of a predefined tolerance, such that by comparison of the offset with the tolerance, an aligned state is indicated when the offset, lateral and/or axial, is within the predefined tolerance. In one example embodiment herein, such functions are performed by a controller (e.g., a data processing unit DPU, and/or controller CONT of FIG. 12 described below). Also in one example embodiment herein, the indicator panel IP is included in the instrument(s) described herein, and is coupled to and controlled by the data processing unit DPU and/or a controller (e.g., controller CONT described below) of the instrument(s). In another example embodiment herein, the indicator panel IP is provided by way of a visual display such as, by example and without limitation, video display unit VDU described below.

Additionally or alternatively to the use of indicator panel IP described above in connection with FIGS. 9A and 9B, automatic mechanical alignment of the objective lens to the subject may be provided, as represented in FIG. 10.

In FIG. 10, the objective lens is mounted in an objective lens barrel OLB which is fixed to a platform P via an objective mount OMU and movable objective stage MOS. Movable objective stage MOS is movable, for example, in an axial direction and/or in a lateral direction. Movable objective stage MOS may, for example, be a motorised XY stage. Objective lens barrel OLB is supported above movable objective stage MOS by, for example, vertical positioning units VPU adapted to raise and lower objective lens barrel OLB relative to platform P. Vertical positioning units VPU may, for example, be motorised screw drives. Platform P is also provided with subject headrest SHR which is fixed to platform P and which has concave portions against which a person A can rest, for example, its forehead and chin so as to stabilise the subject's head in a defined position.

Based on the determined offsets, movable objective stage MOS can be advanced towards or retracted from subject headrest SHR in an axial direction to reduce an axial offset to within a defined tolerance, and alternatively may also be laterally displaced in a horizontal direction to reduce a horizontal axial offset to within a defined tolerance. Similarly, vertical positioning units VPU may be raised or lowered to reduce a lateral offset in a vertical direction to within a defined tolerance. Thereby, an objective lens of objective lens barrel OLB may be correctly positioned relative to the subject to enable proper posterior imaging.

In alternative example embodiment herein, the objective lens barrel OLB may be fixed and, instead, the subject headrest SHR may be automatically displaceable in one or more directions to attain proper positioning by way of similar translation arrangements, based on the determined offsets.

In the above description, it has been explained that an offset between the pupil of the eye is determined by reference to an iris of the eye as an anatomical landmark. However, in other examples herein, other anatomical landmarks can be used as a proxy to infer pupil position. For example, based on typical anatomical dimensions of the eye, the lens, cornea or other anterior structures of the eye can be used as anatomical landmarks for proper positioning of the expected pivot point relative to the pupil. In such a case, either an inferred pupil position can be determined for comparison with the expected position of the pivot point to infer an offset between the pupil position and the expected position of the pivot point, or an expected aligned position of the anatomical landmark can be compared with an actual determined position of the anatomical landmark to determine an offset directly. Simultaneous determination and subsequent use of multiple offsets from multiple landmarks, or a single offset from a best fit of multiple landmarks to an eye mode, may also be performed.

In the above description, it has been explained that alignment processing is performed using a whole axial region corresponding to the interferogram acquired by detector DET. However, in other embodiments herein, coarse alignment of the system may be performed by other techniques and/or mechanisms, and the above-disclosed techniques may be applied to a defined sub-region of an axial region which contains an expected position of a pivot point or pivot plane.

The above disclosure has been explained with respect to an optical coherence tomography instrument which has a switchable objective, which is switchable between a first configuration to allow anterior imaging and a second configuration to allow posterior imaging. However, the present disclosure is not limited to this, and, indeed, an alternative configuration is disclosed in which the objective is settable between the first configuration and the second configuration by movement of the objective in the instrument.

For example, as described above, the objective lens may be axially movable by, for example, the objective lens stage (e.g., movable objective stage MOS) in the instrument, so that the position of the objective relative to a subject may be altered under control of a controller (e.g., data processing unit DPU and/or controller CONT) of the instrument. With such a configuration, the objective lens may be moved between a first defined axial position to allow anterior imaging and a second axial configuration to allow posterior imaging.

For example, the first and second defined axial configurations may be set to have a predetermined axial separation corresponding to a typical axial separation between a pupil and retina in the human eye, namely about 17 mm. Thereby, selection may be made between an anterior imaging modality for alignment of the pivot point and, for example, the pupil of the eye, and a posterior imaging modality for imaging of, for example, the retina, without modifying the internal optical configuration of the objective.

In particular, when an operator of the instrument selects an alignment operation, the controller (e.g., data processing unit DPU and/or controller CONT) may command the stage to move the objective lens to the first defined axial position to perform the alignment operation, and when an operator of the instrument selects an acquisition operation, the controller may command the stage (e.g., movable objective stage MOS) to move the objective lens to the second defined axial position to perform the acquisition operation.

In another example embodiment herein, the objective lens may be manually movable between the first defined axial position and the second defined axial position, for example, by mounting the objective on a linear bearing such as a slider (not shown) arranged between objective lens body OLB and objective mount OMU. To allow precise positioning of the objective lens between the first defined axial position and the second defined axial position, detents located at positions D1 and D2 may be provided at the first and second defined axial position, to provide feedback to an operator that the correct axial position has been reached for each modality. In an alternative embodiment, stops can be provided, rather than or in addition to detents. Where detents are provided, in one example embodiment herein the detents can be configured to require a predefined minimum force to displace the objective from the relevant defined position. Thereby, the detents can function to avoid the objective from being inadvertently displaced from an intended position for each modality. In a further example embodiment herein, a magnetic coupling is arranged at each of first and second defined positions to secure the objective lens at each position.

In still another example embodiment herein, the movable objective lens may be provided with position sensors such as contact sensors, magnetic sensors or optical sensors to detect a position of the objective lens in the instrument, and to detect, in particular, whether the objective lens is set at the first defined position, at the second defined position, or neither. In the configuration shown in FIG. 10, for example, an optical encoder head OLEH can be arranged in the objective mount to face an encoder scale OLES provided to objective lens body OLB to provide information as to the relative position of the objective lens body and mount. When the lens is manually movable, such sensors can be used to signal to a controller (e.g., data processing unit DPU and/or controller CONT) of the instrument that the anterior (alignment) or posterior (acquisition) mode has been selected, and to initiate or permit execution of respective alignment or acquisition routines of the instrument. When the objective lens is movable controllably, such as by the motorised stage, such sensors can be used to signal to a controller (e.g., data processing unit DPU and/or controller CONT) of the instrument that the desired position for anterior or posterior imaging has been reached, such that further motion of the lens can cease.

In the above example embodiment(s), the first and second defined positions have been explained as defined positions in the instrument. However, the first and second defined positions can be defined relative one to another, in some example embodiments herein.

For example, in one embodiment herein, the objective stage (e.g., movable objective stage MOS) may be used under manual or automatic control to move the objective in coarse alignment relative to the patient, for example, using a camera, scale or distance sensor to position the objective lens axially and/or laterally relative to the subject's eye at a first position suitable for a fine alignment process using the anterior imaging modality. The same stage may be used to move the objective lens then axially and/or laterally based on measurements acquired during the fine alignment process to position the pivot point appropriately relative to the pupil of the eye. This position may then be regarded as the first defined position for the anterior imaging, and the stage may then be operated to move the objective lens by a predetermined axial distance to the second defined position for posterior imaging.

In an alternative example embodiment herein, different positioning mechanisms such as linear bearings, sliders or motors can be used to move the objective between the first and second defined positions and to move the objective for other operations. As one example herein, with reference to FIG. 10, a linear bearing for axial movement may be arranged at the objective lens mount OMU between the objective lens OLB and the movable objective stage MOS, and the linear bearing may be used to move the objective lens between the first and second defined positions, whether under manual action by an operator or motorised control by a controller (e.g., digital processing unit DPU and/or controller CONT) of the instrument. As shown in FIG. 10, a motor ODU may be arranged, for example as a screw drive or direct drive to translate the objective lens body OLB relative to the objective mount.

At least some example embodiments have been explained with respect to an optical coherence tomography instrument which has a settable objective, which is settable between a first configuration to allow anterior imaging and a second configuration to allow posterior imaging. However, the present disclosure is not limited to this, and, in other example embodiments herein, an alternative configuration is provided that includes independent anterior and posterior OCT interferometers, which share at least part of a common objective.

One such example embodiment is illustrated in schematic form in FIG. 11, which shows another example embodiment herein of at least one OCT instrument in which a posterior imaging configuration is in relevant respects equivalent to that shown in FIG. 1 and described above in connection therewith. The illustrated embodiment comprises a first swept light source SLS, first reference optical system ROS, first detector DET, first analogue to digital converter ADC, first digital processing unit DPU, first optical beam splitter OBS, and a first sample optical system SOS that can scan a sample beam across one or more predetermined parts of a sample S. According to an example embodiment herein, these components, at least some of which collectively form a first OCT interferometer (also referred to herein as a first interferometer configuration or arrangement), are the same (and operate in the same manner) as the corresponding components described above in connection with FIG. 1, and thus, for convenience, they will not be described herein in further detail.

The example embodiment illustrated in FIG. 11 also comprises an interface optical system IOS and a second OCT interferometer (also referred to herein as a second interferometer configuration or arrangement), wherein the interface optical system IOS is interposed and communicatively coupled between the first and second OCT interferometers. The second OCT interferometer comprises a second swept light source SLS2, second reference optical system ROS2, second detector DET2, second analogue to digital converter ADC2, and second optical beam splitter OBS2. In one example embodiment herein, those components of the second OCT interferometer are similar to corresponding components of the first OCT interferometer.

The second swept light source SLS2 supplies measurement light to the second optical beam splitter OBS2, which splits the light into reference light and a sample light. The reference light is provided to the second reference optical system R0S2 and the sample light is provided to the interface optical system IOS. The interface optical system IOS introduces sample light of the second OCT interferometer (and received from second optical beam splitter OBS2) to the eye via at least part of the sample optical system SOS of the first OCT interferometer. In one example embodiment herein, the interface optical system IOS introduces the sample light to the sample optical system SOS via a further beam splitter arranged inside or outside the objective of the sample optical system SOS.

With respect to the reference light, the second reference optical system ROS2 reflects and returns the reference light to the second optical beam splitter OBS2, with or without a delay caused by the second reference optical system ROS2, depending on the application of interest. At the second optical beam splitter OBS2, returning reflected light of the sample light (i.e., the sample light reflected from the sample S) and the returning reference light (i.e., the reference light returned from the second reference optical system ROS2) are combined so as to interfere with one another and are directed as interfering beams to the second detector DET2. The second detector DET2, which, in one example embodiment herein, is a photodetector such as a photodiode or an avalanche photodiode, converts an optical intensity of the interfering light to provide a resulting converted signal in the form of, for example, an electrical signal such as a voltage or current. In one example embodiment herein, the resulting converted signal is a time-varying analogue signal. After being output by the second detector DET2, the resulting converted signal can be recorded in a time-varying manner, as will be described below, wherein a recorded version of the signal constitutes an interferogram between the returning reflected light and the returning reference light with respect to the optical frequency of the narrowband light from the second swept light source SLS2.

In the example embodiment depicted in FIG. 11, the second analogue to digital converter ADC2 periodically samples and quantises the signal output by the second detector DET2 with a defined (predetermined) sample frequency, and then digital values of the quantised and sampled signal are provided to the data processing unit DPU wherein the values are recorded. In one example embodiment herein, the data processing unit DPU performs a Fourier transform, such as a fast Fourier transform, on the time-varying quantised and sampled signal values obtained from the second analogue to digital converter ADC2 to generate an axial depth profile.

In an example embodiment herein, the interface optical system IOS is configured such that the second OCT interferometer scans (using the sample light) a plane containing the pivot point of the first OCT interferometer, and an amount of optical delay introduced by the second reference optical system ROS2 to the reference light is such that an axial region from which the interferogram obtained by the second interferometer extends across the plane containing the pivot point. For example, the second reference optical system ROS2 may have a fixed optical path length. Thereby, the second OCT interferometer can be used for alignment in a similar manner to the anterior imaging configuration described above, while the first OCT interferometer can be used to obtain images of the retina.

If the OCT interferometers are alternately activated with a suitably fast switching speed, such that light from only one interferometer is applied to the eye at any given time, the interferometers can be used to provide near simultaneous alignment and measurement of the eye. Alternatively, by using swept light sources (e.g., swept light sources SLS and SLS2) having different non-overlapping wavelength sweep bandwidths, and predetermined filtering of the combined light returning from the subject, it is possible to operate both interferometers simultaneously to confirm proper pupil positioning and to obtain OCT measurements of the retina.

In the above description, example embodiments and functionality of an OCT instrument have been described. According to an example embodiment herein, one or more functions of the OCT instrument are performed under automatic or programmatic control by a controller, such as, in one example embodiment herein, data processing unit DPU and/or controller CONT.

FIG. 12 illustrates a schematic block diagram of a controller CONT constructed and operable for controlling functions of one or more OCT instruments, coupled to a video display unit VDU, according to an example embodiment herein. In one example embodiment herein, the controller CONT controls at least some or all of the various components shown in FIGS. 1-6, 9A, 9B, 10, and 11, and also may form all or at least part of the data processing unit DPU, or vice versa. As represented in FIG. 12, all of the components of the controller CONT are coupled to one another and thus can inter-communicate.

Controller CONT comprises a swept signal generator SSG for controlling a sweep of one or more external narrowband swept light sources such as swept light sources SLS and SLS2 (not shown in FIG. 12).

Controller CONT also comprises an interferometer control unit ICU which controls the functions of one or more OCT interferometers, such as the OCT interferometers described above and represented in FIGS. 1 and 11. In example embodiments herein, at least some of the functions include performing phase matching between sample and reference arms of the interferometer(s), for example, by controlling a variable optical delay included in, for example, the reference arm(s).

Controller CONT also comprises a scan control unit SCU which controls a scanning pattern applied to a sample beam (or sample light), for example, by adjusting a speed, angular range and/or mutual phase of one or more scan units, such as scan unit SC1 and scan unit SC2 (not shown in FIG. 12). For example, scan control unit SCU can cause scan unit SC1 and scan unit SC2 to cooperate in deflecting the sample beam (or sample light) to select among available scanning patterns, or to apply an arbitrary scanning pattern. In one example embodiment herein, the scan pattern is a linear scan pattern, in which a line scan along a particular direction is repeatedly scanned. In another example embodiment herein, the scan pattern is a rotating radial scan pattern, in which a line scan is repeated while rotating an angle of the scanning direction about an axial point. In a further example embodiment herein, the scan pattern is a raster scan pattern, in which a line scan in a first direction is progressively advanced in a second direction intersecting with the first direction.

Controller CONT also comprises an analogue to digital converter ADC for receiving, quantizing, and sampling an analogue signal from a detector DET (not shown in FIG. 12), and providing a resulting converted signal in digital form for further processing by one or more of the other components of the controller CONT. By example and without limitation, the converted signal output from analogue to digital converter ADC is transformed by a fast Fourier transform performed by a fast Fourier transform unit FFT to generate an axial depth profile. In an example embodiment herein, the analogue to digital converter ADC of FIG. 12 may form and/or be included in one or more of the analogue to digital converters (e.g., ADC and ADC2) described above, although in other example embodiments a plurality of separate analogue to digital converters ADC and ADC2 are included in the controller CONT, and each may provide a respective converted signal to a same fast Fourier transform unit FFT or to separate respective fast Fourier transform units FFT that, in one example embodiment herein, are included in the controller CONT.

Controller CONT also comprises a tomographic reconstruction unit TRU, which, based on a plurality of axial depth profiles generated by fast Fourier transform unit FFT reconstructs a 2D tomogram or a 3D tomographic dataset. Tomographic reconstruction unit TRU can output, for example, image data corresponding to B-scans or C-scans. Tomographic reconstruction unit TRU is also configured to allow extraction of a slice along one or more directions from a 3D, graphic dataset to extract a 2D tomogram along, for example, an arbitrary plane through the 3D dataset.

Controller CONT also comprises an image processing unit IPU for applying image processing algorithms to image data generated by tomographic reconstruction unit TRU. For example, the image processing unit IPU applies edge detection algorithms to identify boundaries of anatomical features represented in the image data. Controller CONT also comprises a feature extraction unit FEU which operates either on images directly obtained from tomographic reconstruction unit TRU, or on images which have been processed by image processing unit TRU, to identify and extract the positions of particular anatomical features in the images. For example, features and/or positions of a cornea, lens, iris, retina, fovea, optic nerve junction, and other well-known landmarks in the eye can be identified either by correlation with geometrical primitives such as circles, ellipses, triangles, converging or diverging lines in appropriate relationships, or otherwise by pattern-matching using other known feature extraction techniques. Feature extraction unit FEU can also extract positions of one or more such anatomical features in the images extracted.

Controller CONT also comprises an offset determination unit ODU which compares the extracted positions of the anatomical features in the images with reference positions in the images representing a pivot plane or pivot point of an apparent point source projected by an objective lens toward a subject in a posterior imaging configuration. Offset determination unit ODU can extract one or more offsets as vector or scalar values, for example, along particular axes or in particular planes passing through the pivot plane or pivot point.

Controller CONT also comprises a visual display controller VDC which connects to the visual display unit VDU (e.g., of an OCT instrument), and which causes display on the visual display unit VDU of images such as tomograms generated by the tomographic reconstruction unit TRU, processed tomograms generated by the image processing unit IPU and other data. In one example embodiment herein, visual display controller VDC can be configured to combine data from one or more other components or units of the controller CONT, for example, by overlaying on tomograms or image-processed tomograms references indicating the position of the pivot point or pivot plane, markers indicating anatomical features identified and extracted by the feature extraction unit FEU, and values and vectors relating to offsets determined by the offset determination unit ODU. Visual display controller VDU also can be configured to display on the visual display unit VDU operating parameters of the instrument such as a scan pattern selected, a sweep range, as well as diagnostic parameters of the instrument such as signal-to-noise values and stability values.

Controller CONT also comprises an alignment recognition unit ARU. Alignment recognition unit ARU operates on offsets determined by the offset determination unit ODU to determine whether and not the offsets are sufficiently small such that a pupil of the subject may be regarded as properly aligned with an expected position of the pivot point or expected pivot plane. Alignment recognition unit ARU, for example, can apply one or more thresholds to either scale offsets or vector offset components determined by offset determination unit ODU. Alignment recognition unit ARU can provide signals indicating that alignment in one or more directions, axes or planes has been achieved. Visual display controller VDC also can be configured to display indicators based on an alignment state determined by alignment recognition unit ARU.

Controller CONT also comprises subject position controller SPC. Subject position controller SPC provides command signals to other components or elements of the controller CONT and/or OCT instrument employing the controller CONT, based on the alignment status determined by alignment recognition unit ARU and/or the offsets determined by offset determination unit ODU. For example, subject position controller SPC can control, based on the alignment status or the offsets, indicator panel IP, shown, for example, in FIG. 9A and FIG. 9B to provide visual feedback in the above-described manner to the subject as to whether or not alignment has been achieved, and in which direction and by how much the subject should move to bring a pupil into proper alignment with the instrument. Additionally or alternatively, subject position controller SPC can issue drive commands to movable objective stage MOS and/or vertical positioning unit VPU shown in FIG. 10 so as to cause objective lens barrel OLB to move relative to a measurement subject restrained by subject headrest SHR so as to achieve proper alignment.

Controller CONT also comprises an optical system controller OLC for controlling other components of systems/instruments described herein, such as, by example and without limitation, the beam adjustment unit BAU, focus, tilt and shift lenses which may be included in sample optical system SOS, and in particular the switching of the objective lens between the anterior and the posterior measurement configuration, for example by commanding a drive unit to insert or extract additional optical element AOE used to perform the switching.

Controller CONT also comprises a general-purpose memory MEM for short-term or long-term storage and retrieval of data by any other unit or component of the controller CONT, an arithmetic logic unit ALU for performing arithmetical or logical operations on data values supplied by any other unit or component of the controller CONT, a clock generator CLK for generating one or more clocks for synchronising operations of the various units or components of the controller CONT, an input-output controller IOC for interfacing with external devices and/or facilities such as external storage devices, network devices and/or supervisory hardware, as well as operator interface devices such as control panels, keypads, keyboards, touch-panels and pointing devices. The memory MEM may comprise, by example only and without limitation, a RAM, ROM, hard drive, floppy disc, memory stick, a buffer, or the like. In one example embodiment herein, the memory MEM stores instructions and/or programs for performing the methods and functions described herein and represented in the drawings. In other example embodiments, one or more of such memories may be external to the controller CONT and communicatively coupled thereto.

Controller CONT also comprises a main control unit MCU which coordinates the operations of the controller CONT according to predefined operating sequences such as high-level operating programs or in accordance with instructions received from operator interface devices via the input output controller IOC, and which can control other components of the controller CONT. In one example embodiment herein, the master control unit MCU (and/or the arithmetic and logic unit ALU) can read and write data, instructions and programs from/to the memory MEM, and can execute the instructions and programs to perform the methods and functions described herein and represented in the drawings.

Also according to an example embodiment herein, the master control unit MCU and/or the controller CONT may form and/or be included in the data processing unit DPU (or vice versa) of other figures described herein.

Figure 13:
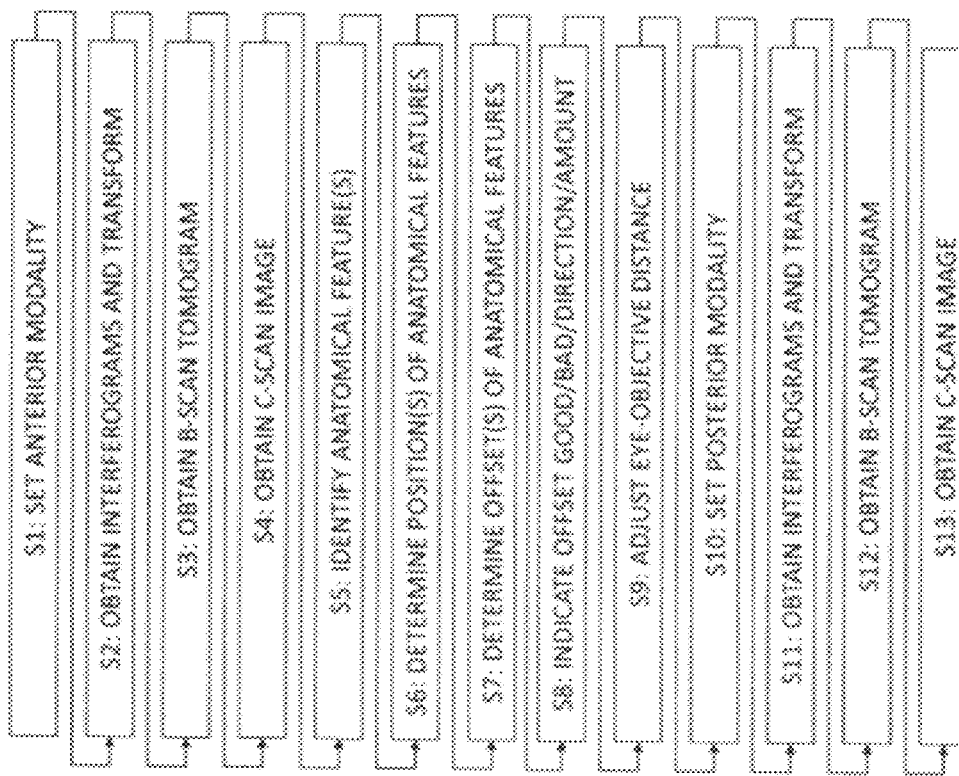
FIG. 13 shows a flow diagram of an optical coherence tomography measurement process incorporating an alignment process, according to an example embodiment herein.

One example operating programme which can, for example, be implemented under control of the controller CONT by executing a predefined operating sequence or a program and/or instructions coordinated by main control unit MCU is shown in FIG. 13. That is, FIG. 13 illustrates a method according to an example embodiment herein. The method can be implemented by one or more individual ones of the optical coherence tomography (OCT) instruments described above and shown in FIGS. 1 and 11.

In a step S1, the anterior imaging modality of a OCT instrument is set, for example by introducing additional optical element AOE into an objective lens of the instrument. In step S1, predetermined focus and beam parameters for the instrument are set by optical system controller OSC, a predetermined sweep bandwidth for (at least one swept light source SLS of) the instrument is set by swept signal generator SSG, and a phase difference between corresponding sample and reference arms of the instrument is determined, specified and/or fixed by interferometer control unit ICU such that an axial region from which an interferogram may be obtained extends across a plane containing a pivot point of, for example, one or more posterior imaging configurations. Moreover, in step S1 a predetermined scan pattern for the instrument is set by the scan control unit SCU, such as, for example, a radial scan pattern or a raster scan pattern centred on an optical axis of at least one objective lens of the instrument(s).

In step S2, the OCT instrument is operated as described herein to obtain one or more interferograms, based on the predetermined scan pattern. In one example embodiment herein, step S2 includes obtaining interferograms repeatedly by scanning a sample beam (light) according to the scan pattern, and using analogue to digital converter ADC (among other components of the instrument) to provide the interferograms.

In step S3, the instrument is operated to obtain one or more B-scan tomograms. By example and without limitation, in step S3 tomograms are obtained for each scan line by transforming the interferograms using a fast Fourier transform FFT (e.g., performed by fast Fourier transform unit FFT of the instrument) and assembling axial depth profiles, thereby generated into one or more tomograms using topographic reconstruction unit TRU of the instrument.

In step S4, the tomograms of a plurality of adjacent scan lines are assembled into a 3D tomographic dataset, and slices of this dataset are extracted to obtain a C-scan image, by operating the instrument.

In step S5, image processing such as a predetermined edge extraction algorithm is applied to the B-scan image and/or the C-scan image, and one or more anatomical features are identified by feature extraction unit FEU of the instrument.

In step S6, feature extraction unit FEU determines one or more positions of one or more anatomical features in the B-scan image and/or the C-scan image, and, from those positions, an expected position of a pupil of an eye of a subject.

In step S7, offset determination unit ODU of the instrument determines offsets of the pupil of the eye from the expected position of the pivot point determined by the optical configuration of the objective lens.

In step S8, alignment recognition unit ARU determines whether or not the offsets are sufficiently small (e.g., within a predetermined tolerance) such as to be considered in alignment, and subject position controller SPC and visual display controller VDC send signals commanding respectively indicator panel IP and the visual display unit VDU to indicate a state and degree of alignment.

In step S9, based on a result of step S8 subject position controller SPC of the instrument commands movable objective stage MOS and/or vertical positioning unit VPU to move the objective lens barrel OLB into proper alignment with the subject, while the subject is restrained by subject headrest SHR, until alignment recognition unit ARU confirms that sufficient alignment has been achieved.

In step S10, optical system controller OLC commands the switching of the objective lens to the posterior configuration, for example, by commanding withdrawal of additional optical element AOE. In other words, in step S10 the instrument is placed in the posterior configuration/mode.

With the pupil of the subject now properly aligned with the pivot point of the posterior imaging configuration, steps S2 to S4 are repeated as steps S11 to S13, respectively, using the posterior configuration to obtain OCT measurements of an interior of a posterior chamber of the subject, for example, images of the retina. In an example embodiment herein, steps S11 to S13 are performed in a similar manner as described above in connection with steps S2 to S4, but while the instrument is operating in the posterior configuration/mode. Step S11 obtains at least one interferogram, step S12 obtains at least one B-scan tomogram, and step S13 obtains at least one C-scan image. After step S13, control can pass back to another one of the steps, such as, by example, step S1 where the method proceeds therefrom in the above-described manner.

It should be noted that, although for convenience only a single data processing unit DPU is shown in FIG. 11, in other example embodiments another data processing unit can be connected to an output of the analogue to digital converter ADC2.

Example aspects herein relate to an optical coherence tomography instrument, a method for operating the instrument, and a computer-readable medium storing a program for performing the method. Those example aspects enable improved and more convenient alignment of a scan pivot point with a pupil of an eye, relative to conventional methods and systems.

In the foregoing description, example aspects are described with reference to several example arrangements. Accordingly, the specification should be regarded as illustrative, rather than restrictive. Similarly, the figures illustrated in the drawings, which highlight the functionality and advantages of the example arrangements, are presented for example purposes only. The architecture of the example arrangements is sufficiently flexible and configurable, such that it may be utilized in ways other than those shown in the accompanying figures.

Software arrangements of the examples presented herein may be provided as a computer program, or software, such as one or more programs having instructions or sequences of instructions, included or stored in an article of manufacture such as a memory, machine-accessible or machine-readable medium, an instruction store, or computer-readable storage device, each of which can be non-transitory, in one example arrangement. The program or instructions on the non-transitory memory, machine-accessible medium, machine-readable medium, instruction store, or computer-readable storage device, may be used to program a computer system or other electronic device. The memory, machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "memory", "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, data processing unit, or computer processor and that causes the machine/computer/unit/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some arrangements may also be implemented by the preparation of application-specific integrated circuits, field-programmable gate arrays, or by interconnecting an appropriate network of conventional component circuits.

Some arrangements include a computer program product. The computer program product may be a memory, storage medium or media, instruction store(s), or storage device(s), having instructions stored thereon or therein which can be used to control, or cause, a computer or computer processor to perform any of the procedures of the example arrangements described herein. The memory/storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the memory, computer-readable medium or media, instruction store(s), or storage device(s), some implementations include software for controlling both the hardware of the system and for enabling the system or microprocessor to interact with a human user or other mechanism utilizing the results of the example arrangements described herein. Such software may include without limitation device drivers, operating systems, and user applications. Ultimately, such memories, computer-readable media or storage device(s) further include software for performing example aspects of the disclosure, as described above.

Included in the programming and/or software of the system are software modules for implementing the procedures described herein. In some example arrangements herein, a module includes software, although in other example arrangements herein, a module includes hardware, or a combination of hardware and software.

While various example arrangements of the present disclosure have been described above, it should be understood that they have been presented by way of example, and not limitation. It will be apparent to persons skilled in the relevant art(s) that various changes in form and detail can be made therein. Thus, the present disclosure should not be limited by any of the above described example arrangements, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example arrangements presented herein in any way. It is also to be understood that any procedures recited in the claims need not be performed in the order presented.

While this specification contains many specific arrangement details, these should not be construed as limitations on the scope of any disclosures or of what may be claimed, but rather as descriptions of features specific to particular arrangements described herein. Certain features that are described in this specification in the context of separate arrangements can also be implemented in combination in a single arrangement. Conversely, various features that are described in the context of a single arrangement can also be implemented in multiple arrangements separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the arrangements described above should not be understood as requiring such separation in all arrangements, and it should be understood that the described program components and systems can generally be integrated together in a single software product or packaged into multiple software products.

Having now described some illustrative arrangements and arrangements, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one arrangement are not intended to be excluded from a similar role in other arrangements or arrangements.

The apparatuses and methods described herein may be embodied in other specific forms without departing from the characteristics thereof. The foregoing arrangements are illustrative rather than limiting of the described systems and methods.

Scope of the apparatuses and methods described herein is thus indicated by the appended claims, rather than the foregoing description, and changes that come within the meaning and range of equivalence of the claims are embraced therein.

The invention claimed is:

1. An ophthalmic optical coherence tomography instrument comprising:
    a light source arranged to generate measurement light;
    a coupler arranged to split the measurement light into reference light and sample light;
    a sample arm, comprising a front-end optical system, and arranged to direct the sample light towards a subject position and to receive reflected sample light from the subject position;

a reference arm, comprising a return optical system, and arranged to receive the reference light and return the reference light to interfere with the reflected sample light; and a detector arranged to detect an interferogram of the reflected sample light and the returned reference light, wherein the front-end optical system comprises a scanner defining an apparent point source for scanning the sample light across the subject position and an objective having a posterior imaging configuration to project the apparent point source onto a pivot point on a pivot plane between the objective and the subject position, and wherein the objective is settable between the posterior imaging configuration for scanning the sample light across a retina of an eye at the subject position and an anterior imaging configuration for scanning the sample light across the pivot plane.

2. The instrument of claim 1, wherein at least one of the sample arm or the reference arm is adjustable to vary an axial region in which the sample light scans across the subject position.

3. The instrument of claim 1, wherein, while the objective is set in the anterior imaging configuration, an axial region in which the sample light scans across the subject position is fixed to extend across the pivot plane.

4. The instrument of claim 1, further comprising a controller arranged to set the objective in one of the posterior imaging configuration or the anterior imaging configuration.

5. The instrument of claim 1, wherein, while the objective is in the anterior imaging configuration, the controller causes the scanner to scan the sample light across the pivot plane, such that a plurality of interferograms from each scan are obtained by the detector and derives a tomogram from the plurality of interferograms.

6. The instrument of claim 5, wherein the instrument comprises a display unit, and wherein the controller is arranged to cause the display unit to display the tomogram.

7. The instrument of claim 6, wherein the controller is arranged to cause the display unit to display a reference indicating a position of the pivot point together with the tomogram.

8. The instrument of claim 5, wherein, while the objective is set in the anterior imaging configuration, the controller causes the scanner to scan the sample light across the pivot plane in a plurality of scans, the plurality of scans extending two-dimensionally across the pivot plane, to obtain a plurality of tomograms.

9. The instrument of claim 8, wherein the plurality of scans comprises one of:
i) a plurality of intersecting scans having intersecting scan directions crossing the pivot plane, or
ii) a plurality of progressive scans progressing across the pivot plane in a direction intersecting with a common scan direction.

10. The instrument of claim 5, wherein, while the objective is set in the anterior imaging configuration, the controller detects a presence of a structure of an anterior segment of the eye within an axial region using the tomogram.

11. The instrument of claim 10, wherein the controller is arranged to recognize the presence of the structure within the axial region, and to actuate an offset indicator based on recognition of the presence of the structure.

12. The instrument of claim 10, wherein the structure includes one of a lens, iris, or cornea.

13. The instrument of claim 5, wherein, while the objective is set in the anterior imaging configuration, the controller detects a presence of a structure of an anterior segment of the eye within a sub-region of an axial region corresponding to a reference region relating to the pivot point.

14. The instrument of claim 5, wherein, while the objective is set in the anterior imaging configuration, the controller obtains a structure position of a structure of an anterior segment of the eye at the subject position using the tomogram.

15. The instrument of claim 14, wherein the controller is arranged to determine an offset between the structure position and a reference position related to the pivot point.

16. The instrument of claim 15, wherein the instrument further comprises an offset indicator for indicating an offset between the structure position and the reference position, and the controller is arranged to actuate the offset indicator based on the determined offset.

17. The instrument of claim 15, wherein the instrument comprises an objective motor for adjusting an axial position of the objective based on the determined offset.

18. The instrument of claim 15, wherein the offset includes an axial offset.

19. The instrument of claim 15, wherein the offset includes a lateral offset.

20. The instrument of claim 1, wherein the objective is axially movable in the instrument from a first defined position for the posterior imaging configuration to a second defined position for the anterior imaging configuration.

21. The instrument of claim 20, wherein the first defined position is defined by a first stop or detent and the second defined position is defined by a second stop or detent, and the objective is movable manually from the first defined position to the second defined position.

22. The instrument of claim 20, wherein the instrument further comprises an objective motor for moving the objective axially, and the controller is arranged to cause the objective motor to move the objective from the first defined position to the second defined position.

23. The instrument of claim 20, wherein the instrument further comprises an objective position detector arranged to detect an axial position of the objective at the first defined position and the second defined position, and the controller is configured to detect movement of the objective from the first defined position to the second defined position using the objective position detector.

24. The instrument of claim 1, wherein the objective is switchable from the posterior imaging configuration to the anterior imaging configuration.

25. The instrument of claim 24, wherein the objective is switchable by inserting an optical element to the objective or removing an optical element from the objective.

26. The instrument of claim 1, wherein the objective is arranged, in the anterior imaging configuration, to project the apparent point source onto another pivot point on another pivot plane arranged between the objective and the pivot plane.

27. The instrument of claim 1, wherein the objective is arranged, in the anterior imaging configuration, as a telecentric lens to scan the sample light from the apparent point source vertically at the pivot plane.

28. The instrument of claim 1, wherein the scanner comprises a first scanning element for scanning the sample light in a first direction, and a second scanning element for scanning the sample light in a second direction, and wherein the front end optical system also comprises a transfer optical system arranged between the first and second scanning elements to generate a two-dimensional scan pattern from an apparent point source at the second scanning element.

29. The instrument of claim 28, wherein the first scanning element is located at a first focal point of the transfer optical system and the second scanning element is located at a second focal point of the transfer optical system.

30. An ophthalmic optical coherence tomography instrument comprising:
a light source arranged to generate measurement light;
a coupler arranged to split the measurement light into reference light and sample light;
a sample arm, comprising a front-end optical system, and arranged to direct the sample light towards a subject position and to receive reflected sample light from the subject position;
a reference arm, comprising a return optical system, and arranged to receive the reference light and return the reference light to interfere with the reflected sample light; and
a detector arranged to detect an interferogram of the reflected sample light and the returned reference light,
wherein the front-end optical system comprises a scanner defining an apparent point source for scanning the sample light across the subject position and an objective having a posterior imaging configuration to project the apparent point source onto a pivot point on a pivot plane between the objective and the subject position,
wherein the objective is settable between the posterior imaging configuration for scanning the sample light across a retina of an eye at the subject position and an anterior imaging configuration for scanning the sample light across the pivot plane, and
wherein the objective is axially movable in the instrument from a first defined position for the posterior imaging configuration to a second defined position for the anterior imaging configuration.

31. The instrument of claim 30, wherein at least one of the sample arm or the reference arm is adjustable to vary an axial region in which the sample light scans across the subject position.

32. The instrument of claim 30, wherein, while the objective is set in the anterior imaging configuration, an axial region in which the sample light scans across the subject position is fixed to extend across the pivot plane.

33. The instrument of claim 30, further comprising a controller arranged to set the objective in one of the posterior imaging configuration or the anterior imaging configuration.

34. The instrument of claim 30, wherein, while the objective is in the anterior imaging configuration, the controller causes the scanner to scan the sample light across the pivot plane, such that a plurality of interferograms from each scan are obtained by the detector and derives a tomogram from the plurality of interferograms.

35. The instrument of claim 34, wherein the instrument comprises a display unit, and wherein the controller is arranged to cause the display unit to display the tomogram.

36. The instrument of claim 35, wherein the controller is arranged to cause the display unit to display a reference indicating a position of the pivot point together with the tomogram.

37. The instrument of claim 34, wherein, while the objective is set in the anterior imaging configuration, the controller causes the scanner to scan the sample light across the pivot plane in a plurality of scans, the plurality of scans extending two-dimensionally across the pivot plane, to obtain a plurality of tomograms.

38. The instrument of claim 37, wherein the plurality of scans comprises one of:

i) a plurality of intersecting scans having intersecting scan directions crossing the pivot plane, or
ii) a plurality of progressive scans progressing across the pivot plane in a direction intersecting with a common scan direction.

39. The instrument of claim 34, wherein, while the objective is set in the anterior imaging configuration, the controller detects a presence of a structure of an anterior segment of the eye within an axial region using the tomogram.

40. The instrument of claim 39, wherein the controller is arranged to recognize the presence of the structure within the axial region, and to actuate an offset indicator based on recognition of the presence of the structure.

41. The instrument of claim 39, wherein the structure includes one of a lens, iris, or cornea.

42. The instrument of claim 34, wherein, while the objective is set in the anterior imaging configuration, the controller detects a presence of a structure of an anterior segment of the eye within a sub-region of an axial region corresponding to a reference region relating to the pivot point.

43. The instrument of claim 34, wherein, while the objective is set in the anterior imaging configuration, the controller obtains a structure position of a structure of an anterior segment of the eye at the subject position using the tomogram.

44. The instrument of claim 43, wherein the controller is arranged to determine an offset between the structure position and a reference position related to the pivot point.

45. The instrument of claim 44, wherein the instrument further comprises an offset indicator for indicating an offset between the structure position and the reference position, and the controller is arranged to actuate the offset indicator based on the determined offset.

46. The instrument of claim 44, wherein the instrument comprises an objective motor for adjusting an axial position of the objective based on the determined offset.

47. The instrument of claim 44, wherein the offset includes an axial offset.

48. The instrument of claim 44, wherein the offset includes a lateral offset.

49. The instrument of claim 30, wherein the first defined position is defined by a first stop or detent and the second defined position is defined by a second stop or detent, and the objective is movable manually from the first defined position to the second defined position.

50. The instrument of claim 30, wherein the instrument further comprises an objective motor for moving the objective axially, and the controller is arranged to cause the objective motor to move the objective from the first defined position to the second defined position.

51. The instrument of claim 30, wherein the instrument further comprises an objective position detector arranged to detect an axial position of the objective at the first defined position and the second defined position, and the controller is configured to detect movement of the objective from the first defined position to the second defined position using the objective position detector.

52. The instrument of claim 30, wherein the objective is arranged, in the anterior imaging configuration, to project the apparent point source onto another pivot point on another pivot plane arranged between the objective and the pivot plane.

53. The instrument of claim 30, wherein the objective is arranged, in the anterior imaging configuration, as a telecentric lens to scan the sample light from the apparent point source vertically at the pivot plane.

54. The instrument of claim 30, wherein the scanner comprises a first scanning element for scanning the sample light in a first direction, and a second scanning element for scanning the sample light in a second direction, and wherein the front end optical system also comprises a transfer optical system arranged between the first and second scanning elements to generate a two-dimensional scan pattern from an apparent point source at the second scanning element.

55. The instrument of claim 54, wherein the first scanning element is located at a first focal point of the transfer optical system and the second scanning element is located at a second focal point of the transfer optical system.

56. An ophthalmic optical coherence tomography instrument comprising:
  a light source arranged to generate measurement light;
  a coupler arranged to split the measurement light into reference light and sample light;
  a sample arm, comprising a front-end optical system, and arranged to direct the sample light towards a subject position and to receive reflected sample light from the subject position;
  a reference arm, comprising a return optical system, and arranged to receive the reference light and return the reference light to interfere with the reflected sample light; and
  a detector arranged to detect an interferogram of the reflected sample light and the returned reference light,
  wherein the front-end optical system comprises a scanner defining an apparent point source for scanning the sample light across the subject position and an objective having a posterior imaging configuration to project the apparent point source onto a pivot point on a pivot plane between the objective and the subject position,
  wherein the objective is settable between the posterior imaging configuration for scanning the sample light across a retina of an eye at the subject position and an anterior imaging configuration for scanning the sample light across the pivot plane, and
  wherein the scanner comprises a first scanning element for scanning the sample light in a first direction, and a second scanning element for scanning the sample light in a second direction, and wherein the front end optical system also comprises a transfer optical system arranged between the first and second scanning elements to generate a two-dimensional scan pattern from an apparent point source at the second scanning element.

57. The instrument of claim 56, wherein the first scanning element is located at a first focal point of the transfer optical system and the second scanning element is located at a second focal point of the transfer optical system.

58. The instrument of claim 56, wherein the objective is settable between the posterior imaging configuration to the anterior imaging configuration by at least one of:
  axially moving the objective in the instrument from a first defined position for the posterior imaging configuration to a second defined position for the anterior imaging configuration; or
  inserting an optical element to the objective or removing an optical element from the objective.

\* \* \* \* \*